(12) United States Patent
Haapasaari et al.

(10) Patent No.: US 7,549,324 B2
(45) Date of Patent: Jun. 23, 2009

(54) CONSISTENCY TRANSMITTER

(75) Inventors: Toivo Johannes Haapasaari, Kajaani (FI); Urpo Ensio Heikkinen, Kajaani (FI); Matti Juhani Laitinen, Kajaani (FI); Heikki Tapio Leinonen, Kajaani (FI); Markku Seppänen, Kuluntalahti (FI); Eero Ossi Antero Tolonen, Kajaani (FI)

(73) Assignee: Kajaanin Prosessimittaukset Oy, Kajaani (FI)

( * ) Notice: Subject to any disclaimer, the term of this patent is extended or adjusted under 35 U.S.C. 154(b) by 217 days.

(21) Appl. No.: 10/572,109

(22) PCT Filed: Sep. 7, 2004

(86) PCT No.: PCT/FI2004/000518

§ 371 (c)(1),
(2), (4) Date: Dec. 6, 2006

(87) PCT Pub. No.: WO2005/026697

PCT Pub. Date: Mar. 24, 2005

(65) Prior Publication Data

US 2007/0193344 A1 Aug. 23, 2007

(30) Foreign Application Priority Data

Sep. 16, 2003 (FI) .................................. 20031321

(51) Int. Cl.
*G01N 11/14* (2006.01)
*G01N 33/34* (2006.01)
*G01N 33/00* (2006.01)

(52) U.S. Cl. ..................... 73/61.41; 73/53.03; 73/54.23; 73/54.28; 73/54.35

(58) Field of Classification Search ................ 73/53.03, 73/54.23, 54.26, 54.27, 54.28, 54.32, 54.33, 73/54.35, 61.41
See application file for complete search history.

(56) References Cited

U.S. PATENT DOCUMENTS 2,992,651 A 7/1961 Krofta (Continued)

FOREIGN PATENT DOCUMENTS

EP 0211112 2/1987

(Continued)

*Primary Examiner*—Daniel S Larkin
(74) *Attorney, Agent, or Firm*—Volpe and Koenig, P.C.

(57) ABSTRACT

The present invention is a consistency transmitter for the measurement of consistency, viscosity, and other properties of matter. The transmitter consists of a measuring element, attached to a bearing-mounted shaft and rotated in the matter to be measured by a direct drive motor that is positioned coaxially with the measuring element and its shaft. The stator of the direct drive motor is integrated into the consistency transmitter body, its rotor into the shaft. The stator is coaxially attached to a first flange that transmits the torsional force of the motor with flexible elements to a second flange positioned on the shaft. The first and second flanges are attached to differential elements with which the phase angle between the flanges is measured using measuring elements located near the flanges. The shaft of the measuring element is bearing-mounted inside a tubular torsion shaft. The consistency transmitter can be inserted into an operating process by means of special installation equipment consisting of a shut-off valve combined with an insertion pipe. The insertion pipe includes regulating elements in such a way that they match with the matching elements on the transmitter body. With the help of regulating elements and matching elements, the transmitter can be inserted to the desired depth in the process.

20 Claims, 5 Drawing Sheets

U.S. PATENT DOCUMENTS

| | | |
|---|---|---|
| 3,572,086 A | 3/1971 | Johnston .................... 73/54.32 |
| 3,826,476 A | 7/1974 | Ahrenberg |
| 4,375,047 A | 2/1983 | Nelson et al. |
| 4,829,811 A | 5/1989 | Ehlert et al. |
| 5,627,330 A | 5/1997 | Preikschat et al. ......... 73/866.5 |
| 6,571,609 B1 * | 6/2003 | Bi ............................. 73/54.31 |

FOREIGN PATENT DOCUMENTS

| | | |
|---|---|---|
| EP | 1 260 808 A1 | 11/2002 |
| FI | 40128 B | 6/1968 |
| GB | 733541 | 7/1955 |

* cited by examiner

CONSISTENCY TRANSMITTER

BACKGROUND OF THE INVENTION

The object of the present invention is a consistency transmitter for the measurement of consistency, viscosity, and other such characteristics of matter. The object of the invention is particularly the consistency analyzers used in the pulp and paper industry.

In rotary consistency transmitters known in the prior art, a measuring element is rotated in the process being measured. Fibers and filler particles present in the measured matter, such as papermaking pulp, tend to resist the rotary motion of the measuring element. This resisting force, which is proportional to the shear force generated by the process matter, is measured using various torque measurement techniques and further converted into a variable indicating consistency. In prior art solutions the measuring element is rotated by a single-phase or three-phase motor that is located to the side of the rotation axis. The motor is connected to the torsion shaft by gear, chain, or belt drive transmission or some other power transmission system. Gearing is required in order to reduce the rotation speed. The use of single-phase or three-phase motor to rotate the measuring element poses several problems and limitations.

A three-phase motor suited for process conditions weighs from 6 to 10 kg, a single-phase motor over 10 kg. The motor has to be installed to the side of the torsion shaft, and thus the shaft forms a lever arm and the heavy motor causes a strong flexural and torsional stress at the point of the attachment to the process pipeline. Especially in process pipeworks, support structures must be installed, and these increase the investment cost. The bending and torsion caused by the weight of the motor also puts a strain on the torsion shaft. The weight of the motor and the required massiveness of the transmitter structure results in that the entire device may weigh over 30 kg. Thus, handling of the device requires several people or a hoist.

Power transmission elements require regular service and thus cause maintenance costs. For example, a transmission belt must be inspected for wear every six months and replaced every few years. The transmission belt causes extra bending strain on the torsion shaft and will thus contribute to more rapid wear of bearings and mechanical seals.

The rotation speed of single-phase and three-phase motors is dependent on the mains network frequency. The torque resisting the rotation of the measuring element increases exponentially as a function of both consistency and rotation speed of the measuring element. When the measuring element is rotated at a constant speed, its shape must be selected in accordance with the properties of the measured medium. The defining of suitable measuring elements causes additional costs and also increases the number of necessary spare parts.

Motor load, and thus also rotation speed, varies due to a number of reasons. Changes in rotation speed cause the measurement signal to drift and thereby complicate the measurement. Rotation speed changes when consistency, i.e. the shear force resisting measuring element rotation, changes. The rotation speed changes also due to changes in the friction of the torsion shaft bearings and mechanical seals. The friction forces in mechanical seals are affected by process pressure: a higher pressure forces the sealing surfaces more tightly against each other and thus increases friction. In cage induction motors, the backward slip that affects rotation speed is also dependent on motor load.

Most cage induction motors have a fixed direction of rotation, and as consequence, unwanted materials caught to the measuring element can only be removed if the device is first pulled out of the process.

Single-phase and three-phase motors require high-voltage operating power and must be well enclosed to protect them from moisture and the process environment. High voltage increases electrical safety requirements, and a qualified electrician is needed to install a three-phase motor to the power network or to disconnect it. Several single-phase and three-phase operating voltages are known in the world, and thus a separate motor type has to be chosen for each voltage. The need to provide for different operating voltages increases the variety of models and spare parts that a manufacturer has to offer.

SUMMARY OF THE INVENTION

An object of the present invention is to provide a consistency transmitter where the measuring element is rotated by a direct drive motor. The rotor of the direct drive motor is coaxially attached to the torsion shaft of the measuring element, while its stator is attached to the support structure of the torsion shaft in such a way that the rotor and stator are coaxial. The direct drive motor is driven by control electronics in such a way that its rotation speed can be changed with a program. The torque caused by the process matter is transmitted along the shaft to a differential element, which consists of two coaxial flanges between which a phase shift resisted by spring elements is generated. Spring elements are attached in pairs to the flanges so that the phase shift is resisted by several pairs of spring elements. Each spring element pair is balanced so as to ensure that the phase shift will be directly proportional to the torque effective over the measuring element and measurable by using opto-electronic or electromagnetic device.

The condition of the bearings, seals, and other elements of the consistency transmitter can be monitored by observing the power consumption of the direct drive motor. The input power of the motor is consumed by the friction of the device's mechanical parts such as bearings and seals of the torsion shaft and by the rotation of the measuring element. The input power of the measuring element can be calculated from its torque, and when this input power is reduced from the total output, the result gives the power required to rotate the torsion shaft. The calculated input power of the torsion shaft will increase for example when bearings are worn or defective, and if this value exceeds a preset limit, the operator can be alerted.

The consistency transmitter can be installed into an operating process, and its insertion distance is adjustable. The drive shaft and the torsion shaft inside it are sealed in such a way that process medium cannot get in touch with the seal ring between the shafts. This sealing arrangement eliminates the effects of process medium on the seals and their friction.

A direct drive motor weighs less than 1 kg and thus causes an essentially smaller flexural strain than the motors according to the prior art. The entire consistency transmitter is a lightweight device that is easy to handle and install, even by a person working alone.

A direct drive motor does not include separate power transmission elements, e.g. belt or belt pulleys, to rotate the measuring element. The load on the bearings is substantially smaller, as the forces caused by power transmission are clearly lower. A direct drive motor can be integrated into the consistency transmitter, and its rotating parts can be balanced with regard to the rotating shaft.

The speed of a direct drive motor can be set to a desired level with a program. Constant feedback of motor rotation speed is obtained, and control electronics keep the rotation speed constant. With one variable stabilized, a more accurate measurement signal is obtained. For optimal consistency measurement it is advantageous, if the speed of the measuring element can be selected so that the desirable speed can be used in each measurement application. For example at high consistencies the rotating speed can be reduced, so as to expand the consistency measuring range of a measuring element. Freely selectable rotating speed means that only one measuring element is needed in order to measure consistency throughout the consistency range used in the pulp and paper industry, typically from 0.5% through 16%.

Unwanted materials (e.g. plastic shreds) may be present in the process and when these get caught to the measuring element, they cause errors in the measurement reading. By reversing the rotation direction, materials caught to the measuring element can be loosened without uninstalling the entire transmitter from the process. Moreover, the verification of the measuring element's zero point or automatic zero point calibration can be done by rotating the measuring element back and forth. If the measuring element is symmetrical, its zero point is the average of the torque readings measured when it is rotated back and forth; if it is asymmetrical, the zero point is between these torque readings. The zero point is specific for each measuring element and can be determined by means of laboratory tests. In some applications calibration can be carried out during operation by placing a calibration brake on the end of the rotation axis of the measuring element.

A direct drive motor's operating voltage is low, e.g. 48 V, which is advantageous as for its electrical safety. The cabling costs of a low-voltage power supply are considerably lower. Moreover, the electrotechnical components of a direct drive motor can be assembled in the same housing as the measurement electronics of the device, which reduces the investment and maintenance costs.

The present invention solves the problems listed above and corrects shortcomings of the prior art. It brings about a direct-drive powered consistency transmitter that is lightweight, easily controlled by program, has a low operating voltage, and is economical in total costs.

The above-mentioned advantages will be achieved by using a consistency transmitter according to the invention characterized by the features described in the independent claims.

The object of the invention is a consistency transmitter for the measurement of consistency, viscosity, and other characteristics of matter. The transmitter consists of a measuring element attached to a bearing-mounted shaft, which measuring element is rotated in the matter being measured. The measuring element is rotated by a direct drive motor that is positioned coaxially with the measuring element and its shaft. The stator of the direct drive motor is integrated into the body of the consistency transmitter, its rotor into the shaft. The rotor is connected to a first flange positioned coaxially with it, by which flange the torsional force of the motor is guided to the second flange on the shaft. The elements between the flanges function as torsional force transmission elements. Differential elements in connection with the first and second flanges indicate the phase angle between them. Close to the flanges there are means for measuring the phase angle between the flanges. The shaft of the measuring element is bearing-mounted inside a tubular torsion shaft. The drive shaft in turn is bearing-mounted inside the transmitter body and sealed at its front end to prevent the entry of process medium inside the device. The drive shaft is sealed in such a way that it can be lubricated and cooled with either water the pressure of which is higher than process pressure or with low-pressure circulating water. In connection with the torsion shaft are also means for sealing, which prevent the entry of process medium inside the transmitter. The task of the torsion shaft is to move the differential elements and their measuring elements further away from the process of variable temperatures. The coupling between torsion shaft and differential elements mechanically protects the differential elements against shocks and overload situations. In addition, the torsion shaft serves to eliminate from the measurement the torque losses caused by the friction of bearings and sealings. The measuring shaft has a small diameter in order to reduce its torque loss. The body of the consistency transmitter is elongated in shape so as to ensure that the measuring element can be inserted sufficiently far into the process. The consistency transmitter can be inserted into an operating process by using dedicated installation equipment. The installation equipment consists of a shut-off valve combined with an insertion pipe. The insertion pipe contains regulating elements that correspond with matching elements on the transmitter body. With the help of the regulating and matching elements, the transmitter can be inserted into the required depth in the process. The insertion distance of the transmitter can be changed while the process is operating, and it can be secured in position by using suitable locking elements.

BRIEF DESCRIPTION OF THE DRAWINGS

In the following the present invention will be described in more detail by some advantageous embodiments and with reference to the attached drawings.

DETAILED DESCRIPTION OF THE PREFERRED EMBODIMENTS

Figure 1:
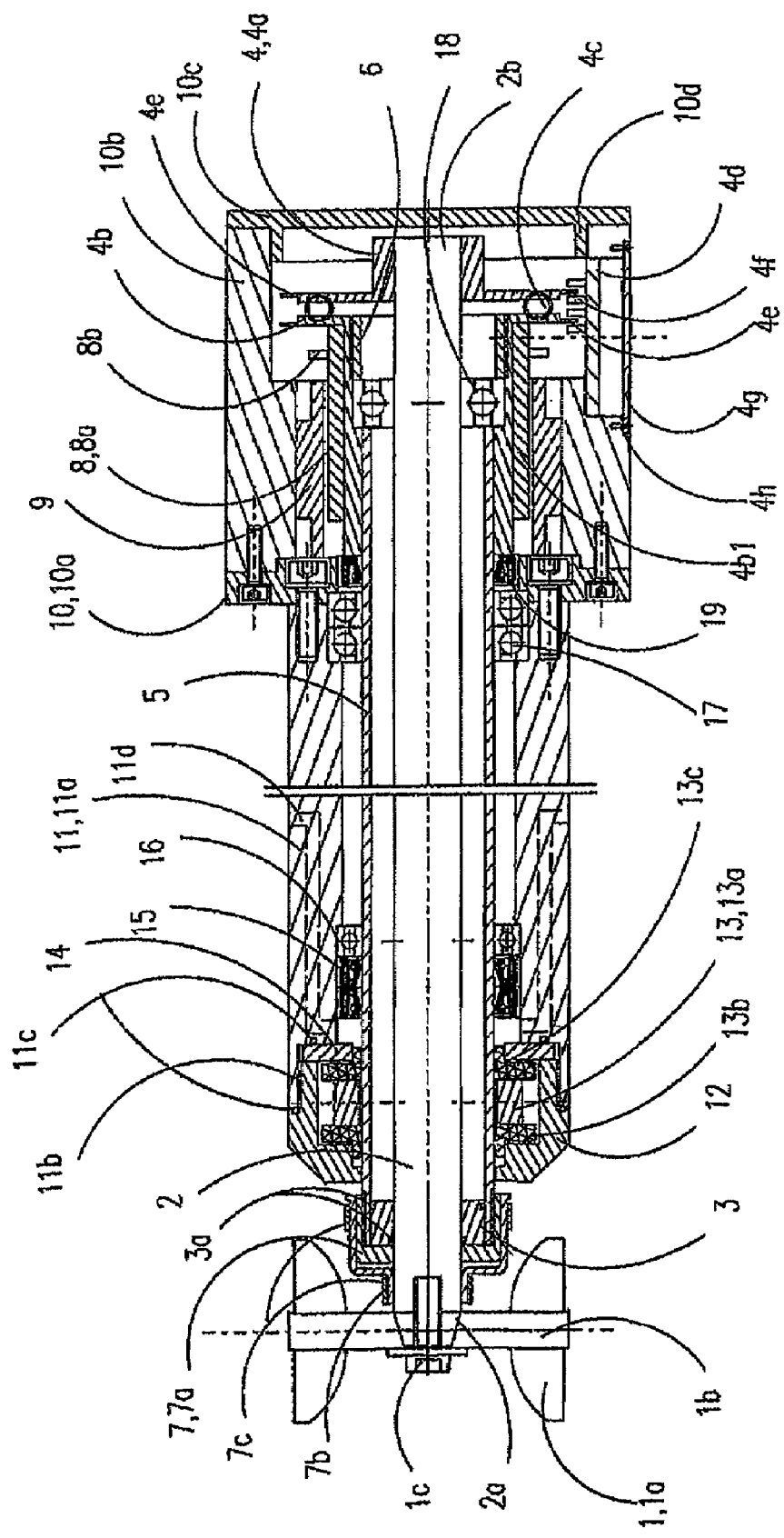
FIG. 1 shows a consistency transmitter according to the invention, in side view and in cross section.
Figure 2:
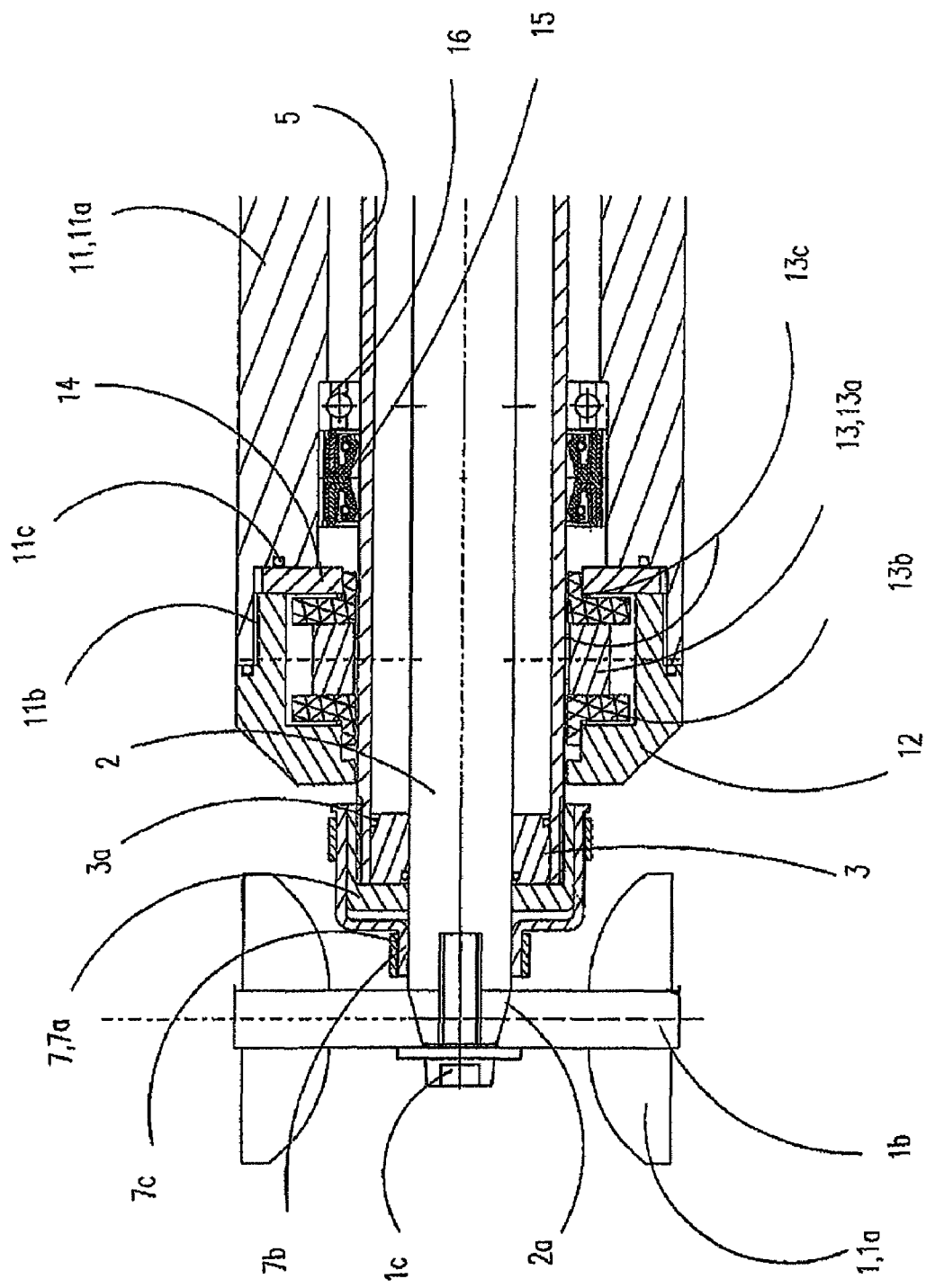
FIG. 2 shows a cross section of the measuring head of the device illustrated in FIG. 1.
Figure 3:
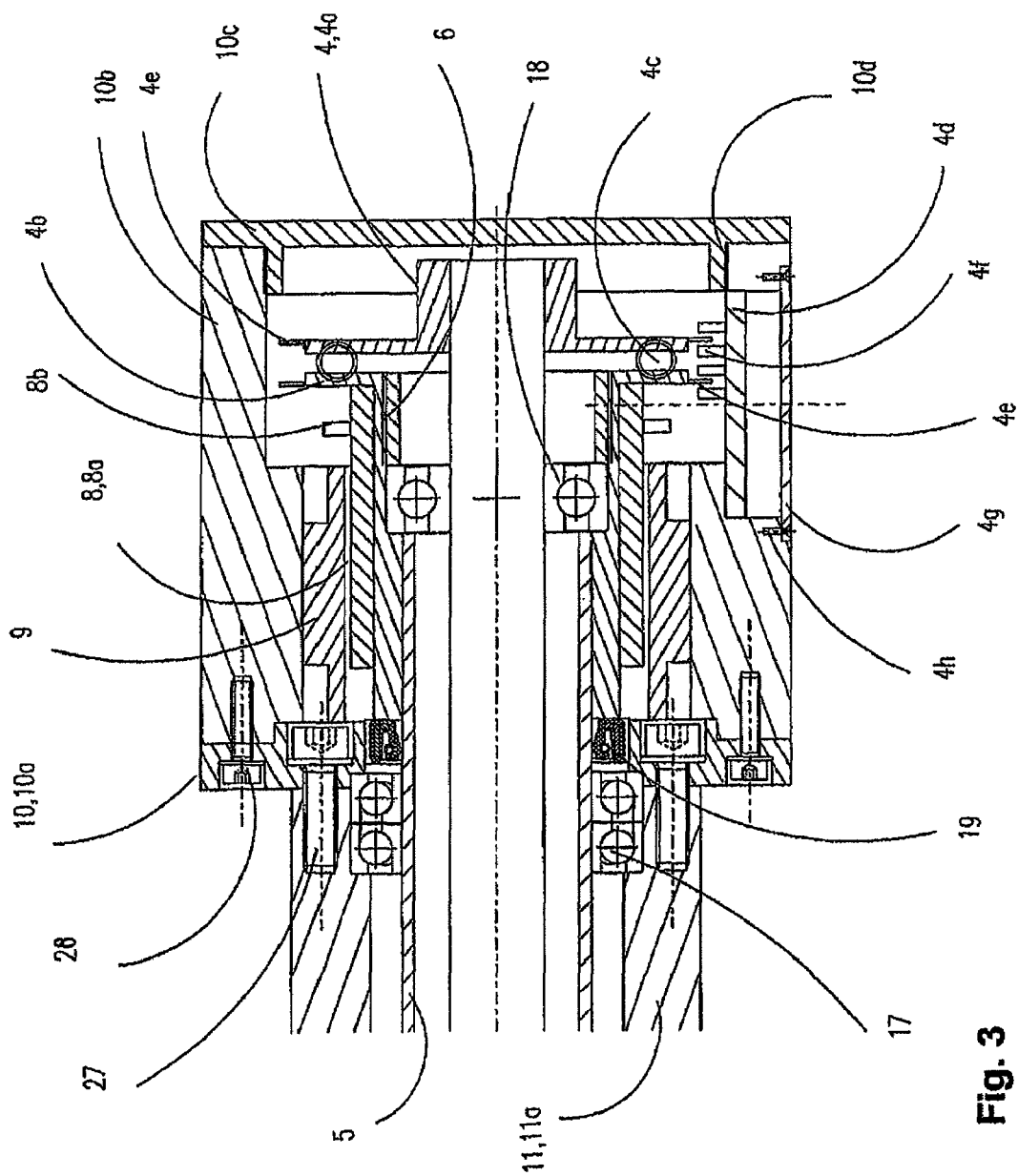
FIG. 3 shows a cross section of the drive end of the device illustrated in FIG. 1.
Figure 4:
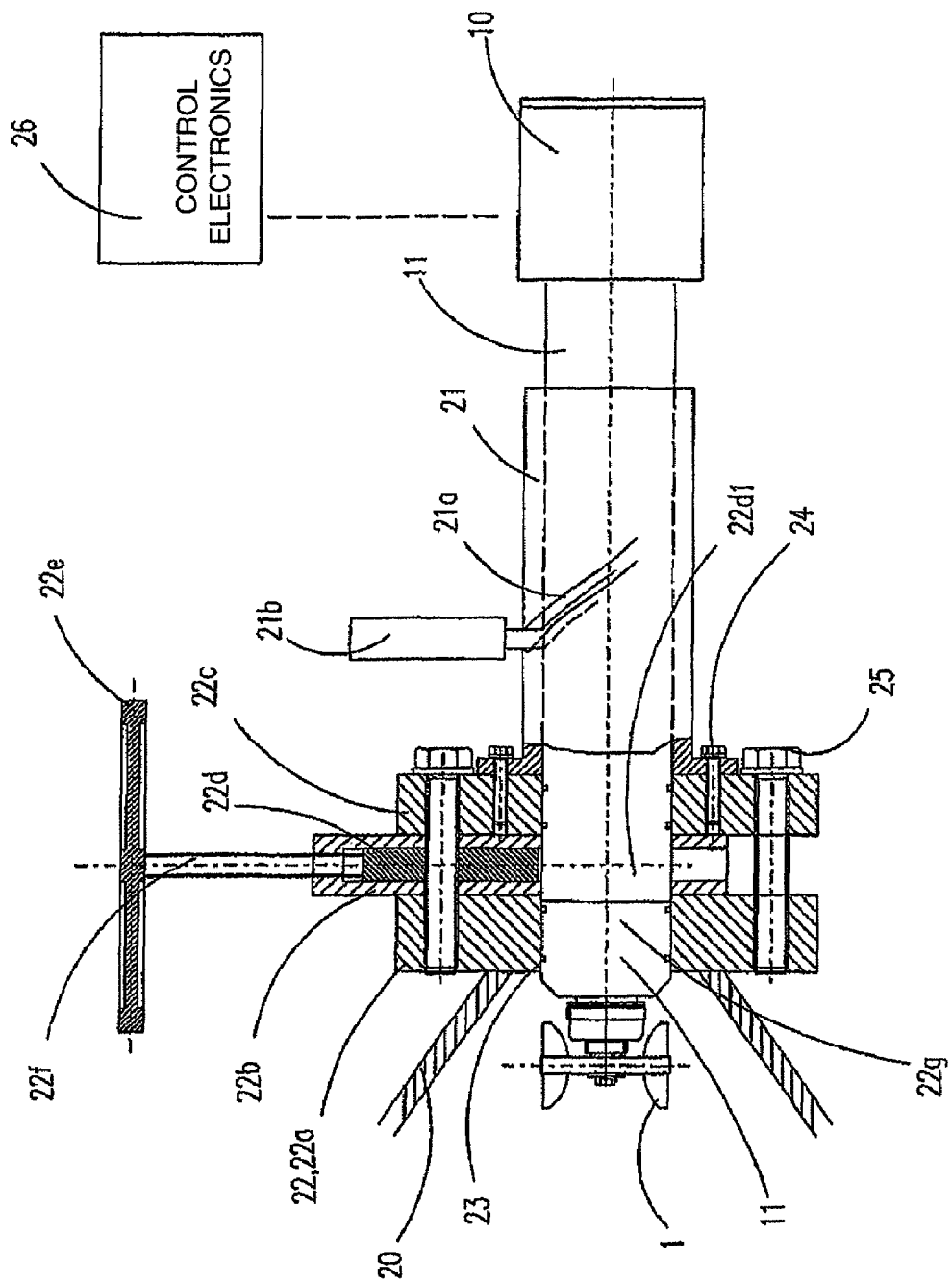
FIG. 4 shows one possible method with which a device according to the invention can be inserted into a process.

FIGS. 1-5 illustrate a consistency transmitter according to the invention, which consists of measuring element 1: torsion shaft 2; bearing and sealing element 3; differential elements 4; drive shaft 5; clamping element 6; clamping and sealing elements 7; rotor 8; stator 9; stator base 10; drive shaft body 11; end piece of drive shaft body 12; sealing elements 13; flange 14; sealing elements 15 and 19; bearing elements 16, 17 and 18; coupling element 20, insertion pipe 21; valve 22; sealing elements 23 and clamping elements 24 and 25; control electronics 26; and calibration equipment 27.

Measuring element 1 consists of motion-resisting elements 1a attached to arms 1b. Measuring element 1 is attached with mounting element 1c to the end 2a of the torsion shaft 2, which is preferably self-centering. Torsion shaft 2 is bearing-mounted inside drive shaft 5, using bearing and sealing element 3 at the measuring end and bearing element 18 at the drive end 2b, which element is advantageously an annular ball bearing. The outer shell of bearing 18 matches with the shoulder of sleeve 4b1 located on the first flange of the differential element, and is axially locked into the shoulder with clamping element 6, which is advantageously a threaded sleeve. Element 3, either slide bearing or roller bearing, is combined with sealing elements 3a to prevent the entry of process media into the device. Calibration equipment 27, including pulling groove 27a, are incorporated in the end of the torsion shaft. A calibration brake (not shown) can be inserted into groove 27a via hole 27b through part 10c, As shown in FIG. 5.

To the drive end 2b of torsion shaft 2 is attached the second flange 4a of the differential element 4, the flange including a slot plate 4e. Slot plates 4e, located on the outer shells of flanges 4a and 4b, consist of a thin plate with a great number of radial slots (not shown). The first flange 4b of differential element 4 is located next to sleeve 4b1, which is positioned coaxially inside rotor 8, so that flanges 4a and 4b and thus also slot plates 4e face each other. Flexible elements 4c, e.g. springs, located between flanges 4a and 4b transmit the torsional force from rotor 8 to torsion shaft 2. Differential elements 4 include elements 4f with which the tangential phase shift between slot plates 4e can be measured. The elements 4f are advantageously suitable opto-electronic or electromagnetic sensors, the signal of which is converted with electronic control devices 26 to correspond to the currently effective torque. Elements 4f are attached to plate 4d which in turn is attached to stator body 10. Plate 4d is inserted through a hole on stator body, and the hole is closed with cover 4g and clamping elements 4h.

Figure 5:
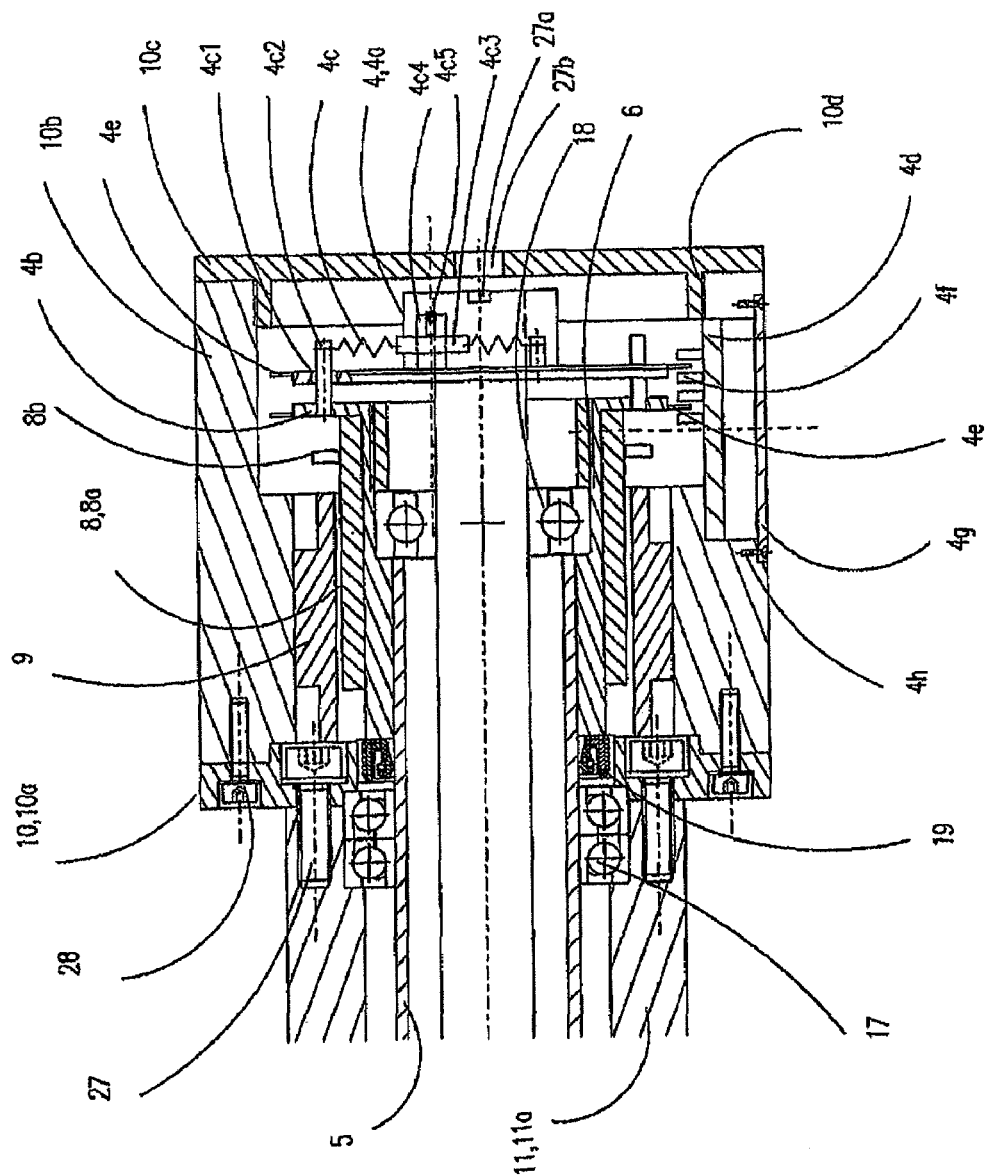
FIG. 5 shows the differential elements and calibration equipment of one application of the present invention.

In one advantageous embodiment of the invention, as shown in FIG. 5, flexible elements 4c are mounted on pins 4c2 that are fastened to flange 4b. Pins 4c2 are parallel with the longitudinal axis of the device, and they protrude through holes 4c1 in flange 4a so far that flexible elements 4c can be fastened to their ends. Flexible elements 4c are connected at their second ends in pairs to slide element 4c3 that is placed between them, which slide element passes through fixing pin 4c4 located on flange 4a. Flexible elements 4c are first connected to pins 4c1 and to slide element 4c3, which will then settle in a balanced state as determined by elements 4c. The slide element is then locked to mounting pin 4c4 with clamping element 4c5. Flexible elements 4c are positioned in such a way that they can receive and attenuate the phase shift generated between flanges 4a and 4b. Holes 4c1 in flange 4a are sufficiently large in diameter so as not to hinder said phase shift. Holes 4c1 and pins 4c2 passing through them act as mechanical overload protection, protecting differential elements 4 from excessive stress. In an overload situation, pins 4c2 will receive stroke-like stress when hitting against the edges of holes 4c1.

Drive shaft 5 is ad advantageously tubular in shape so that torsion shaft 2 can be positioned inside it. Drive shaft 5 is bearing-mounted in the drive shaft body 11 with bearing elements 16 and 17. Element 16 is advantageously an annular ball bearing, and element 17 consists of a pair of angular contact ball bearings. Bearing elements 16 and 17 are sealed with sealing elements 15 and 19. Element 15 advantageously consists of two facing radial seals, element 19 of one radial seal. Element 15 seals the device against process media and also seals the bearing lubricant inside. Element 19 prevents the entry of lubricant inside differential element 4. At its drive end, shaft 5 is also sealed against process medium with sealing elements 13 that are located in the end piece of drive shaft body 12.

Drive shaft 5 is closed at the measuring head end with a sleeve-shaped clamping element 7 attached to the shaft. Clamping element 7 is enclosed by an elastic shell 7b secured with clamping elements 7c that are placed over clamping element 7 and shaft 2. The clamping elements 7c are for example locking rings. Shell 7b is elastic between fastening elements 7c and thus allows the phase shift that the measured torque generates between drive shaft 5 and torsion shaft 2.

The rotor 8 of the direct drive motor is attached on the outer shell of sleeve 4b1 of the first differential element flange using friction mounting or mechanically closed form joint. The rotor includes ring 8a, which contains direct drive motor control devices 8b that are controlled with control electronics 26. Stator 9 is located inside stator base 10 that is positioned coaxially with the rotor. Rotor 8, stator 9, and control devices 8b are advantageously components of a commercially available frameless, brushless direct drive motor.

Stator base 10 consists of a sleeve-shaped body 10b that is enclosed using covers 10a and 10c. Enclosed cover 10c closes the base at the drive end and is attached with fastening element 10d, advantageously a thread. Cover 10a at the measuring head side is centered and fastened to body 10b with elements 28. Also drive shaft body 11 is attached with elements 27 to the opposite side of cover 10a. Cover 10a limits in axial direction bearing element 17, and the above-mentioned sealing element 19 is mounted against its inner shoulder. If necessary, cooling elements such as ribs or channels (not shown) can be arranged onto the outer shell of stator base 10b.

Drive shaft body 11 consists of an elongated and sleeve-like part 11a that is closed at the end by the end piece 12 of drive shaft body. When the device is installed to process, the outer surface of part 11a functions as a sealing surface. Sealing elements 11c are located between end piece 12 and part 11a, and end piece 12 is fastened to the body 11 with fastening element 11b. The fastening element 11b is advantageously a thread. Part 11a is provided with channels for sealing water or for other cooling and cleaning medium.

End piece 12 contains process medium sealing elements 13 that consist of ring 13a and rings 13b that limit it in both directions. Ring 13a rotates with drive shaft 5 while rings 13b remain static, whereby the facing surfaces of rings 13a and 13b provide the sealing effect. Rings 13a and 13b are made of materials suitable for end face seals.

Rings 13a and 13b are sealed against drive shaft 5, end piece 12 and flange 14 using sealing elements 13c. Annular flange 14 is located between drive shaft body 11 and end piece 12.

Installation elements include coupling element 20, insertion pipe 21, valve 22, sealing elements 23, and clamping elements 24 and 25. Coupling element 20 is advantageously a conical sleeve that can be fastened to process pipes of different sizes. Part 20 is fastened to valve 22 that consists of a first flange 22a and a second flange 22c, between which the closing element body 22b is placed. Flanges 22a and 22c are fastened to each other with elements 25, which are advantageously screws. The consistency transmitter can be inserted into hole 22g that passes through the flanges. Hole 22g, and the body of consistency transmitter drive shaft 11, are sealed with sealing elements 23. Closing device 22d, located inside the closing element body, can be moved using arm 22f and handle 22e. The arm 22f is advantageously a threaded bar and the handle is a handwheel or other corresponding device. Closing element 22d is sealed between flanges 22a and 22c with suitable sealing methods (not shown) and includes plate 22d1 that closes hole 22g passing through flanges 22a and 22c. The valve closes when the closing plate 22d1 is moved so that it fully coincides with hole 22g. Insertion pipe 21 is attached to second flange 22c with elements 24, and the consistency transmitter (body 11) can be pushed through the insertion pipe into an operating process. Pipe 21 is provided with pitched grooves 21a that reach all the way to the end of pipe 21 and function as regulating elements. A torsion arm 21b, attached to body 11, travels inside each groove and functions as the matching element of the regulating elements. Insertion pipe 21 is sufficiently long to ensure that body 11 closes hole 22g when valve 22 is open. Torsion arm 21b, traveling in groove 21a, receives the axial force caused by process pressure when the consistency transmitter is being installed to process or removed from it.

In one advantageous embodiment of the invention, the regulating element is thread 21a constructed on the outer shell of body 11, while pegs 21b placed in the thread act as the matching elements. Insertion pipe 21 is split longitudinally so that it can be clamped around the outer shell of body 11 using clamping collars (not shown). The consistency transmitter can then be steplessly screwed deeper into the required distance by using for example a trapezoidal thread 21a.

One device according to the invention functions as follows: Consistency transmitter is inserted into insertion pipe 21 in such a way that torsion arm 21b is in groove 21a. Torsion arm 21b is turned in the groove until the transmitter body 11 is deep enough to close hole 22g. Valve 22 is opened, and the axial force caused by the process pressure will be effective on the transmitter. Torsion arm 21b is turned further, and the transmitter moves against process pressure. The torsion arm is turned until the device reaches the required insertion depth in the process, after which it is secured in position with locking devices (not shown). The consistency transmitter can be extracted from process in reverse order. The transmitter is operated by means of control and automation equipment that is advantageously located in a separate housing. A direct drive motor (8, 9) rotates the measuring element 1 at a program-selectable rotation speed that is set and controlled by control electronics 26 according to the prevailing process conditions. The rotation of measuring element 1 can also be reversed with a program for cleaning or calibration purposes. Torque is transmitted from drive shaft 5 to torsion shaft 2 through flexible elements 4c located between flanges 4a and 4b. The process medium resists the rotation and causes a phase shift, dampened by elements 4c, between torsion shaft 2 and drive shaft 5. This phase shift is measured with the help of slot plates 4e of differential elements using opto-electronic or electromagnetic devices, and it is further converted by a program into a signal corresponding to the measured variable, such as consistency. Drive shaft 5 rotates at the speed of the direct drive motor, receiving the loss torque caused by bearings 16 and 17 and sealings 13, 15 and 19, which thus cannot affect the measurement results. In demanding process conditions this loss torque can be relatively large. Thus the measured phase shift includes the torque generated by the process medium and the losses caused by the torsion shaft bearing and sealing elements (3a, 18, 7b). These losses are very small, as the relative motion of the torsion shaft and the elements in contact with it is small. Said losses can also be reduced by dimensioning the torsion shaft so that its diameter is as small as possible.

The drawings and description are only intended to illustrate the present invention. Its details may vary within the limits set by the attached claims and by the description of the invention. For example, the structure of sealing elements 13 may differ from that described above, depending on the manufacturer. Moreover, it is clear to the man skilled in the art that embodiments of the invention may vary within the operating environment, customer needs, and solutions adopted in manufacturing.

The invention claimed is:

1. Consistency transmitter capable of measuring the consistency and viscosity of matter, comprising a measuring element fastened to an end of a torsion shaft, a drive shaft, differential elements connecting the torsion shaft and drive shaft to each other, and an insertion pipe and valve combined with the insertion pipe for the purpose of inserting the consistency transmitter into a process to be measured while said process is operating, wherein:
    a motor of the consistency transmitter comprises a direct drive stator and rotor, rotation axes of which are coaxial with the rotation axes of the measuring element, torsion shaft, differential elements, drive shaft and the insertion pipe, whereby the consistency transmitter has no separate motor; instead the stator is integrated into a stator base and the rotor is integrated into drive shaft, so that the drive shaft also functions as a rotor shaft;
    the drive shaft is fit with drive shaft bearings on a drive shaft body and the drive shaft bearings are also arranged to act as rotor bearings;
    the drive shaft and the rotor have common covers and seals;
    the drive shaft is comprised of one piece and comprises an end that protrudes into the process being measured; and
    the torsion shaft is bearing-mounted inside the drive shaft.

2. The consistency transmitter according to claim 1, wherein:
    the consistency transmitter is arranged to be inserted into a pressurized process using installation equipment comprising a shut-off valve and the insertion pipe combined with the consistency transmitter; and
    the consistency transmitter is arranged to be inserted to a required depth into the pressurized process, and its depth is arranged to be adjusted by regulating elements and their matching elements on a transmitter body.

3. The consistency transmitter according to claim 2, wherein:
    the drive shaft is closed at a measuring head end with a sleeve-shaped element around which an elastic shell is secured with clamping elements placed over the element and over the torsion shaft, in order to prevent process matter from entering a bearing element and at least one sealing element of the drive shaft; and
    said elastic shell is flexible so as to allow a phase shift between drive shaft and torsion shaft.

4. The consistency transmitter according to claim 2, wherein in a drive end of the torsion shaft is a pulling groove to which a calibration brake is arranged to be attached in order to calibrate the consistency transmitter while the process is operating.

5. The consistency transmitter according to claim 2, wherein a maintenance of the drive shaft bearings and seals is arranged to be monitored by measuring a power transmitted by the rotor and stator, which power is arranged to be compared with an input power of the measuring element so as to detect changes taking place in a condition of the drive shaft bearings and seals.

6. The consistency transmitter according to claim 1, wherein:
    the drive shaft is closed at a measuring head end with a sleeve-shaped element around which an elastic shell is secured with clamping elements placed over the element and over the torsion shaft, in order to prevent process matter from entering a bearing element and at least one sealing element of the drive shaft; and
    said elastic shell is flexible so as to allow a phase shift between the drive shaft and the torsion shaft.

7. The consistency transmitter according to claim 6, wherein in a drive end of the torsion shaft is a pulling groove to which a calibration brake is arranged to be attached in order to calibrate the consistency transmitter while the process is operating.

8. The consistency transmitter according to claim 2, wherein a rotation of the measuring element is arranged to be program-controlled with control electronics according to the needs of each process, and a plurality of motion-resisting elements of measuring element are arranged in such a way that a consistency measurement range of a consistency transmitter provided with said measuring element is from 0.5 to 16%; and
- a rotation speed of the measuring element is arranged to be adjusted according to a process matter, either before or during the process;
- a rotation direction of the measuring element is arranged to be repeatedly reversed in order to free the measuring element from disturbing particles; and
- the rotation direction of the measuring element is arranged to be repeatedly reversed in order to calibrate a signal generated by the measuring element.

9. The consistency transmitter according to claim 6, wherein a rotation of the measuring element is arranged to be program-controlled with control electronics according to the needs of each process, and a plurality of motion-resisting elements of measuring element are arranged in such a way that a consistency measurement range of a consistency transmitter provided with said measuring element is from 0.5 to 16%; and
- a rotation speed of the measuring element is arranged to be adjusted according to a process matter, either before or during the process;
- a rotation direction of the measuring element is arranged to be repeatedly reversed in order to free the measuring element from disturbing particles; and
- the rotation direction of the measuring element is arranged to be repeatedly reversed in order to calibrate a signal generated by the measuring element.

10. The consistency transmitter according to claim 6, wherein a maintenance of the drive shaft bearings and seals is arranged to be monitored by measuring a power transmitted by the rotor and stator, which power is arranged to be compared with an input power of the measuring element so as to detect changes taking place in a condition of the drive shaft bearings and seals.

11. The consistency transmitter according to claim 1, wherein in a drive end of the torsion shaft is a pulling groove to which a calibration brake is arranged to be attached in order to calibrate the consistency transmitter while the process is operating.

12. The consistency transmitter according to claim 11, wherein a rotation of the measuring element is arranged to be program-controlled with control electronics according to the needs of each process, and a plurality of motion-resisting elements of measuring element are arranged in such a way that a consistency measurement range of a consistency transmitter provided with said measuring element is from 0.5 to 16%; and
- a rotation speed of the measuring element is arranged to be adjusted according to a process matter, either before or during the process;
- a rotation direction of the measuring element is arranged to be repeatedly reversed in order to free the measuring element from disturbing particles; and
- the rotation direction of the measuring element is arranged to be repeatedly reversed in order to calibrate the signal generated by the measuring element.

13. The consistency transmitter according to claim 11, wherein a maintenance of the drive shaft bearings and seals is arranged to be monitored by measuring a power transmitted by the rotor and stator, which power is arranged to be compared with an input power of the measuring element so as to detect changes taking place in a condition of the drive shaft bearings and seals.

14. The consistency transmitter according to claim 1, wherein a rotation of the measuring element is arranged to be program-controlled with control electronics according to the needs of each process, and a plurality of motion-resisting elements of the measuring element are arranged in such a way that a consistency measurement range of the consistency transmitter provided with said measuring element is from 0.5 to 16%; and
- a rotation speed of the measuring element is arranged to be adjusted according to a process matter, either before or during the process;
- a rotation direction of the measuring element is arranged to be repeatedly reversed in order to free the measuring element from disturbing particles; and
- the rotation direction of the measuring element is arranged to be repeatedly reversed in order to calibrate a signal generated by the measuring element.

15. The consistency transmitter according to claim 14, wherein a maintenance of the drive shaft bearings and seals is arranged to be monitored by measuring a power transmitted by the rotor and stator, which power is arranged to be compared with an input power of the measuring element so as to detect changes taking place in a condition of the drive shaft bearings and seals.

16. The consistency transmitter according to claim 1, wherein a maintenance of the drive shaft bearings and seals is arranged to be monitored by measuring a power transmitted by the rotor and stator, which power is arranged to be compared with an input power of the measuring element so as to detect changes taking place in a condition of the drive shaft bearings and seals.

17. The consistency transmitter according to claim 1, wherein:
- flexible elements that are part of the differential elements are fastened to pins attached to a second flange;
- said pins are parallel to a longitudinal axis of the consistency transmitter and protrude through holes in a first flange so far that flexible elements can be attached to their ends; and
- at respective second ends thereof, the flexible elements are connected as pairs to a slide element between them, the slide element being arranged to pass through a fixing pin on the second flange in such a way that the slide element is in a balanced state determined by elements.

18. The consistency transmitter according to claim 17, wherein the flexible elements are positioned in such a way that they receive a torsion strain generated between the first and second flange by the consistency and viscosity, of the matter acting on the measuring element ; this strain creates a measurable phase shift, directly proportional to a torsional force, between said flanges.

19. The consistency transmitter according to claim 18, wherein the holes and the pins passing through them are arranged so as to act as overload protection, whereby said pins receive the strain as they collide against edges of the holes.

20. The consistency transmitter according to claim 17, wherein the holes and the pins passing through them are arranged so as to act as overload protection, whereby said pins receive the strain as they collide against edges of the holes.

* * * * *